US011776674B2

(12) United States Patent
Poirier et al.

(10) Patent No.: US 11,776,674 B2
(45) Date of Patent: Oct. 3, 2023

(54) VERIFICATION SYSTEM FOR PRESCRIPTION PACKAGING AND METHOD

(71) Applicant: RX-V INC., Boucherville (CA)

(72) Inventors: Frederic Poirier, Boucherville (CA); Alain Goulet, Mirabel (CA)

(73) Assignee: RX-V INC., Boucherville (CA)

( * ) Notice: Subject to any disclaimer, the term of this patent is extended or adjusted under 35 U.S.C. 154(b) by 52 days.

(21) Appl. No.: 17/111,748

(22) Filed: Dec. 4, 2020

(65) Prior Publication Data

US 2021/0090704 A1 Mar. 25, 2021

Related U.S. Application Data

(63) Continuation of application No. 13/582,878, filed as application No. PCT/CA2011/050129 on Mar. 4, 2011, now abandoned.

(60) Provisional application No. 61/366,649, filed on Jul. 22, 2010, provisional application No. 61/310,896, filed on Mar. 5, 2010.

(51) Int. Cl.
    *G16H 20/13* (2018.01)
(52) U.S. Cl.
    CPC .................. *G16H 20/13* (2018.01)
(58) Field of Classification Search
    CPC ........ G06V 20/66; G06V 10/16; G06V 10/24; G06V 2201/06; G06T 15/20; G06T 2207/10012; G06T 7/0004; G06T 7/33; G06T 7/593; A61J 7/0069; A61J 7/0084; A61J 7/0454; B65B 5/103; G06Q 10/087; B65D 2577/2083; B65D 75/36; B65D 75/527; B65D 75/5888

USPC .......................................................... 348/92
See application file for complete search history.

(56) References Cited

U.S. PATENT DOCUMENTS

| 4,991,223 | A | 2/1991 | Bradley |
| 5,522,512 | A | 6/1996 | Archer et al. |
| 5,963,664 | A | 10/1999 | Kumar et al. |
| 6,535,637 | B1 * | 3/2003 | Wootton ................ G06V 20/66 |
| | | | 221/102 |
| 6,543,692 | B1 | 4/2003 | Nellhaus et al. |
| 6,574,580 | B2 | 6/2003 | Hamilton |

(Continued)

FOREIGN PATENT DOCUMENTS

| CA | 2248204 A1 | 9/1997 |
| WO | 0225568 A2 | 3/2002 |

*Primary Examiner* — Masum Billah
(74) *Attorney, Agent, or Firm* — NORTON ROSE FULBRIGHT CANADA LLP

(57) ABSTRACT

A system for verifying medication doses in a filled medication package comprises an imaging unit to produce at least one image of a filled medication package and a verification unit for receiving the image of the filled medication package. The verification unit comprises a dose locator to determine from the image a location of any dose in the filled medication package, and associate a time period to the location. It also comprises a dose verifier to verify an identity of any dose from the visual characteristics of the image as a function of dose reference profiles. The verification unit compares an identity and time period of the doses of the filled medication package to a prescription and has an interface for producing verification output based on the comparison of the verification unit. A method for verifying medication doses in a filled medication package is also provided.

19 Claims, 3 Drawing Sheets

(56) References Cited

U.S. PATENT DOCUMENTS

| | | |
|---|---|---|
| 6,771,369 B2 | 8/2004 | Rzasa et al. |
| 7,028,723 B1 | 4/2006 | Alouani et al. |
| 7,317,525 B2 | 1/2008 | Rzasa et al. |
| 7,792,349 B2 | 9/2010 | Van Den Brink |
| 7,971,414 B1 | 7/2011 | McGonagle et al. |
| 8,583,281 B2 | 11/2013 | Bear et al. |
| 8,627,639 B2 | 1/2014 | Ali et al. |
| 2001/0033685 A1* | 10/2001 | Ishiyama ............... G06V 40/16 382/274 |
| 2005/0224510 A1 | 10/2005 | Remis et al. |
| 2005/0279419 A1 | 12/2005 | Tribble et al. |
| 2006/0124656 A1 | 6/2006 | Popovich, Jr. |
| 2007/0000939 A1 | 1/2007 | Vasiadis |
| 2007/0265880 A1 | 11/2007 | Bartfeld et al. |
| 2008/0000979 A1 | 1/2008 | Poisner |
| 2008/0056556 A1 | 3/2008 | Eller et al. |
| 2008/0119958 A1 | 5/2008 | Bear et al. |
| 2008/0149657 A1 | 6/2008 | Kim |
| 2009/0014458 A1* | 1/2009 | Heffron ................ A61G 12/001 221/2 |
| 2009/0245681 A1 | 10/2009 | Kobayashi |
| 2009/0299522 A1 | 12/2009 | Savir et al. |
| 2010/0274391 A1 | 10/2010 | Dai |

\* cited by examiner

VERIFICATION SYSTEM FOR PRESCRIPTION PACKAGING AND METHOD

CROSS-REFERENCE TO RELATED APPLICATION

The present application is a continuation of U.S. Non-Provisional Application Ser. No. 13/582,878 filed on Apr. 15, 2013 which is a National Stage Entry of PCT/CA11/50129 filed on Mar. 4, 2011, which claims priority on U.S. Provisional Patent Application No. 61/310,896, filed on Mar. 5, 2010, and U.S. Provisional Patent Application No. 61/366,649, filed on Jul. 22, 2010, both incorporated herein by reference.

FIELD OF THE APPLICATION

The present application relates to medication prescription packaging such as medication trays and dosage systems filled with medication as a function of personal prescriptions, and more particularly to the verification of the contents of medication trays and like dosage systems.

BACKGROUND OF THE ART

Medication trays, blister packs and like dosage systems are useful tools for people having to take a variety of medications on a daily basis. As an example of dosage control packaging, medication trays typically consist of a tray having a plurality of compartments. Each compartment defines a period of a day, and is thus filled with the medication tablets and pills that must be taken at that period. The compartments are individually closed with a backing sheet, thereby forming an assembly known as a blister card. The medication trays are commonly divided into 7 rows of 4 compartments, each row representing a day of the week, and each compartment of a row representing a time of day.

Considering that the medication trays are filled with a large quantity of pills and tablets, and considering that improper doses of medication can be harmful to individuals, great care is currently taken to ensure that medication trays are filled in accordance with a prescription. One verification step may be done by a pharmacy attendant, who visually inspects each compartment and compares the contents to a printed prescription. This is a time-costly process, and even requires in some regions the involvement of the pharmacist, because of regulations.

Similarly, medication packaging (e.g., dosage systems, bulk containers) may contain the incorrect tablets and/or doses, whereby packaging must often be verified manually to ensure the precision of the prescription.

SUMMARY OF THE APPLICATION

It is therefore an aim of the present application to provide a novel verification system for medication packaging.

Therefore, in accordance with a first embodiment, there is provided a system for verifying medication doses in a filled medication package, comprising an imaging unit to produce at least one image of a filled medication package; a verification unit for receiving the image of the filled medication package, and comprising: a dose locator to determine from the image a location of any dose in the filled medication package, and associate a time period to the location; a dose verifier to verify an identity of any dose from the visual characteristics of the image as a function of dose reference profiles, whereby the verification unit compares an identity and time period of the doses of the filled medication package to a prescription; and an interface for producing verification output based on the comparison of the verification unit.

Further in accordance with the first embodiment, a visual characteristics database provides the dose reference profiles to the dose verifier.

Still further in accordance with the first embodiment, the dose reference profiles comprise visual characteristics in the form of at least one of an outline, a geometry, pattern, color data, marking, code pertaining to a specific dose.

Still further in accordance with the first embodiment, the dose reference profiles also comprise data pertaining to at least one of a name, a reference number, a posology of the specific dose.

Still further in accordance with the first embodiment, the verification unit comprises a scan reader for at least one of providing dose location data to the dose locator, and for identifying a dose.

Still further in accordance with the first embodiment, a patient prescription database for providing prescription profiles is provided, and the dose verifier compares the filled medication package to a prescription profile for an identified patient.

Still further in accordance with the first embodiment, the verification unit obtains the dose reference profile related to the prescription, and further wherein the dose verifier verifies the identity of any dose by comparing the dose to the obtained dose reference profile.

Still further in accordance with the first embodiment, an image database for storing the image for the prescription is provided.

Still further in accordance with the first embodiment, the imaging unit comprises actuators to displace a camera to produce multiple images of the filled medication package.

Still further in accordance with the first embodiment, the imaging unit provides coordinates of the camera for each of the multiple images, and the dose locator determines from the coordinates the intake period for doses in the images.

In accordance with a second embodiment, there is provided a method for verifying medication doses in a filled medication package as a function of a prescription, comprising: obtaining at least one image of the filled medication package; determining an intake period of at least one dose from the at least one image; identifying the at least one dose using visual characteristics of the dose from the image in comparison with dose reference profiles; comparing the identity and the intake period of the at least one dose with a prescription; and outputting data related to the comparing.

Further in accordance with the second embodiment, obtaining at least one image comprises obtaining at least two images and creating at least one of a three-dimensional image and a mosaic for subsequent steps.

Still further in accordance with the second embodiment, determining the intake period comprises identifying a compartment of the dose in the filled medication package and associating a day and hour value to the compartment.

Still further in accordance with the second embodiment, determining the intake period comprises reading location data related to a compartment of the dose in the filled medication package.

Still further in accordance with the second embodiment, a patient posologic profile related to the prescription is obtained, and comparing comprises comparing the identity and the intake period of the at least one dose with the patient posologic profile.

Still further in accordance with the second embodiment, dose reference profiles for medication indicated in the patient posologic profile is obtained, and identifying the at least one dose from the image comprises comparing the visual characteristics of the dose with data of the obtained dose reference profiles.

Still further in accordance with the second embodiment, the at least one image with the prescription is stored.

Still further in accordance with the second embodiment, outputting data comprises indicating to an operator an error requiring additional verification.

Still further in accordance with the second embodiment, obtaining at least one image of the filled medication package comprises obtaining coordinates of a camera producing the image, and determining an intake period comprises determining the intake period using the coordinates.

DESCRIPTION OF THE PREFERRED EMBODIMENTS

Figure 1:
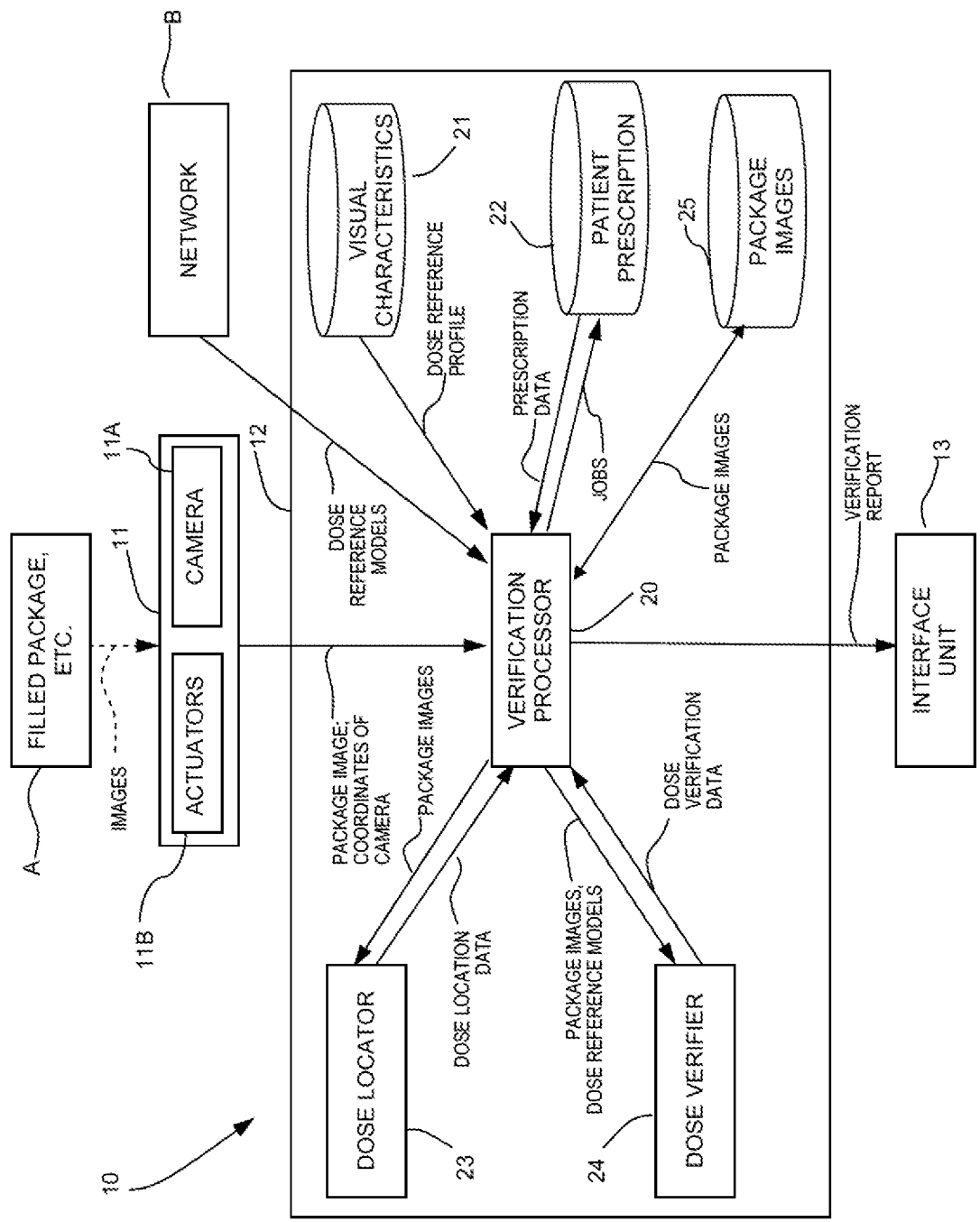
FIG. 1 is block diagram of a verification system for medication packaging in accordance with an embodiment of the present application.

Referring to FIG. 1, a verification system for medication trays is generally shown at 10, with respect to a filled medication package A. The medication package A may be any type of package enclosing medication, such as medication trays, tubular containers, pill packs, blister card or pack, bulk container, PCI controlled dosage system, Pharmacard™, vials, or any other medication packaging. The verification unit 12 is efficiently used with medication packages of the type having a plurality of doses of medication, arranged in separate compartments as a function of a patient posologic profile. For simplicity purposes, reference will be made to a medication package A or filled package A hereafter, but the disclosure is intended to cover uses of the verification system 10 with any appropriate type of medication packages, provided the use is in accordance with the present disclosure. Moreover, reference is made hereafter to the filled package A as comprising pills, with pills referring to any geometrically defined medication doses (as opposed to liquids, powder), such as tablets, capsules, hard gelatin capsules, etc.

The verification system 10 has an imaging unit 11, a verification unit 12, and an interface unit 13.

The imaging device 11 obtains images of the filled medication package A.

The verification unit 12 compares the images to data related to a prescription, and performs a verification.

The interface unit 13 outputs a verification report in any appropriate format, as will be described hereinafter.

The imaging unit 11 is typically a high-resolution digital camera 11A or digital cameras (e.g., 3CCD camera), that are oriented to take global images of the filled package A. In an embodiment, the imaging unit 11 comprises a camera 11A positioned above the filled package A to take a plan view of the filled package. As the medication packages such as medication trays and blister cards may have compartments that are relatively large, a plan view may be sufficient to show all tablets and pills for subsequent identification. The camera produces an image of the tablets. It may be required to lay all tablets manually to ensure that at least a full plan view of each tablet may be obtained, or to use a temporary tray to ensure proper images of laid tablets are taken.

Alternatively, it may be sufficient to obtain an image of a tablet partially obstructed by an adjacent tablet. Therefore, the image of the tablet defines at least a partial outline of the tablet, preferably as naturally lying on a flat surface, but alternatively in any given orientation, in addition to the color (e.g., tint and contrast). The image may also contain ornamentation of the tablet, such as a brand name. The image of the tablet may also comprise an image of a barcode on the tablet. For instance, some tablets may have on their surface a data matrix (a.k.a., two-dimensional matrix barcode), which data matrix represents full tablet information. Other types of coding may be used as well.

The imaging unit 11 may comprise more than one camera, for instance to obtain images from different viewpoints.

The imaging unit 11 may also be mounted to actuators 11B, to move to different points of view. For instance, the imaging unit 11 may be mounted to translation joints, such as linear actuators, for instance as part of a planar manipulator or robot. According to an embodiment, at least one image of each compartment of the filled package A is obtained, with coordinates of the camera 11A being tagged with the image by the monitoring of the actuators 11B. It may also be considered to take multiple images of each single compartment, to obtain different focusing and ensure that the doses will ultimately be identified.

By having multiple images, 2-D mosaics or 3-D images of the pills and tablets may subsequently be produced. The 3-D images are suited for verifying the contents of smaller containers, in which the tablets and pills are randomly packed in height (as opposed to in a plane for the filled package A), such as in a tubular container.

As mentioned above, the digital cameras or equivalent image-producing devices of the imaging unit 11 may also obtain color and tint information from the pills and tablets, for the subsequent identification of the pill/tablet. Accordingly, the imaging unit 11 may comprise its own lighting unit, to ensure that suitable lighting is provided to obtain a clear contour of the pills/tablets. Moreover, the wavelength of the light produced by the imaging unit 11 may be controlled to ensure that the correct color is reflected back to the digital camera of the imaging unit 11. The wavelength used by the imaging unit 11 may replicated the wavelength used to image profile pictures of pills.

The verification unit 12 receives the images of the filled package A or other container from the imaging unit 11, and verifies the contents of the package A in comparison with a patient prescription. The verification unit 12 comprises a verification processor 20 that is typically a processing unit of a computer (PC, laptop, etc) and will run the verification application. It is considered to use an efficient processor (e.g., quad-core processor, among others) to efficiently perform the verification.

The verification processor 20 accesses a visual characteristics database 21, that contains data pertaining to the visual characteristics of the pills and tablets (hereinafter doses). Accordingly, each dose has a dose reference profile, by which each dose is identified in the database 21 with a full identification (name, reference number, posologic data), along with an outline, a geometry, a pattern, color data, marking (brand, name, trademark) or a code (e.g., barcode, data matrix, etc). The geometry may consist in a three-dimensional model of the dose, or in a plurality of flat elevation models (e.g., for instance as laid on a flat surface). In the case where the imaging unit 11 has a single camera, the dose reference profile may have outline models of the dose for all possible orientations. The dose reference profile comprises enough information to differentiate doses from one another.

In an embodiment, medicaments each have a dose reference profile as provided by the manufacturer of the medicament, as detailed hereafter. Alternatively, the dose reference profiles may be created by the operator of the verification system 10, or downloaded from an external source B. In creating the images of the dose reference profiles and in verifying medication packages with the system 10, similar lighting and background conditions may be used.

The verification processor 20 also accesses a patient prescription database 22. The prescription database 22 comprises prescription data for a client/patient. The prescription data is an identification of the doses that must be taken by the client/patient at specific time periods. The jobs featuring the prescription data may be obtained from a pharmacy network B (i.e., LAN, or remote pharmacy server), may be downloaded from another source, or may be programmed, stored and updated in the verification system 10. The patient file may be identified by the verification processor 20 using any information obtained from the images (e.g., bar code, data matrix, characters for OCR), or following manual steps of identification by the operator (e.g., scanning, manual entry of patient id). The verification processor 20 may therefore comprise a scan reader to read such codes from the image obtained from the imaging unit 11.

When package images are obtained, a dose locator 23 of the verification unit 12 provides dose location data for each dose identified from the package images. More specifically, each detected dose is tagged with location data pertaining to the compartment in which the dose is detected, i.e., day and period of the day. The dose locator 23 may identify the location data as a function of the coordinates of the camera 11A of the imaging unit 11 if an actuator is used to move the imaging unit 11, and/or as a function of the position of images of the doses on the image sensor of the imaging unit 11 (as matched with a grid pattern related to the type of packages being scanned), and/or as a function of data manually entered or scanned, among possibilities. Therefore, each imaged dose has coordinates related to location data, and thus related to the posologic profile.

With the package imaged, the dose verifier 24 of the verification unit 12 may identify the dose, using the dose reference models from the characteristics database 21. Each dose is identified by the name of the medication and posologic data, by comparing the visual attributes (geometry, shape, color, marks, barcode, data matrix) of the dose images and the dose reference models of the database 21.

In an embodiment, the dose verifier 24 uses the patient data from the patient prescription database 22 to obtain the dose reference profiles 21 of the doses that are expected per intake period, as per the patient profile. Accordingly, instead of performing an identification of an image dose among a vast number of images, the dose verifier compares the expected dose reference profiles to the dose images. Such a comparison reduces the processing to be performed by the verification processor 20 to verify images, and confirm the identify of the doses.

Therefore, the verification processor 20 combines the dose identification with the location data for each dose, whereby an actual list of doses is produced for the filled medication package A being verified. The actual list of doses is compared with the prescription data for the medication package, namely the desired list of doses per intake time for the medication package. The verification processor 20 produces a verification report through the interface unit 13 providing the comparison data. Accordingly, the verification report may be a confirmation that the actual list of doses is exact and corresponds to the patient prescription. The verification report may indicate that some doses are in excess in given compartments, or alternatively that some doses are missing from given compartments. The verification report may also provide some error messages, requiring a visual inspection by the pharmacy attendant in the event that the package image provides insufficient visual data for some doses, or that some doses do not match any dose reference model. Considering the risks related to improper prescription, the verification steps performed by the verification system 10, and the verification report must be precise and accurate, and any potential error must be reported to the pharmacy attendant/pharmacist.

An image database 25 may be used to keep the images of each package A verified by the verification processor 20, with for instance the data related to the verification. The files in the image database 25 may be used for subsequent verification.

The interface unit 13 may be a printer, a monitor, data output (e.g., in the form of a file data for network communication), and/or any other suitable interface. Accordingly, the interface unit 13 outputs the verification report in any appropriate format, such as a printout, a result screen, an email, a file, etc.

The verification system 10 may perform other tasks related to identifying the filled medication package A.

For instance, the imaging unit 11 may obtain patient data from the medication package A. For instance, the imaging unit 11 may have a bar code reader, and the medication package A may have a bar code representing the patient. The verification unit 12 may thus automatically obtain the patient prescription from the database 22 if the patient is identified with the imaging unit 11. Also, the verification system 10 may be used to quantify the amount of a same dose in a package, as described briefly above when enumerating the various packages A with which the verification system 10 may be used.

Figure 2:
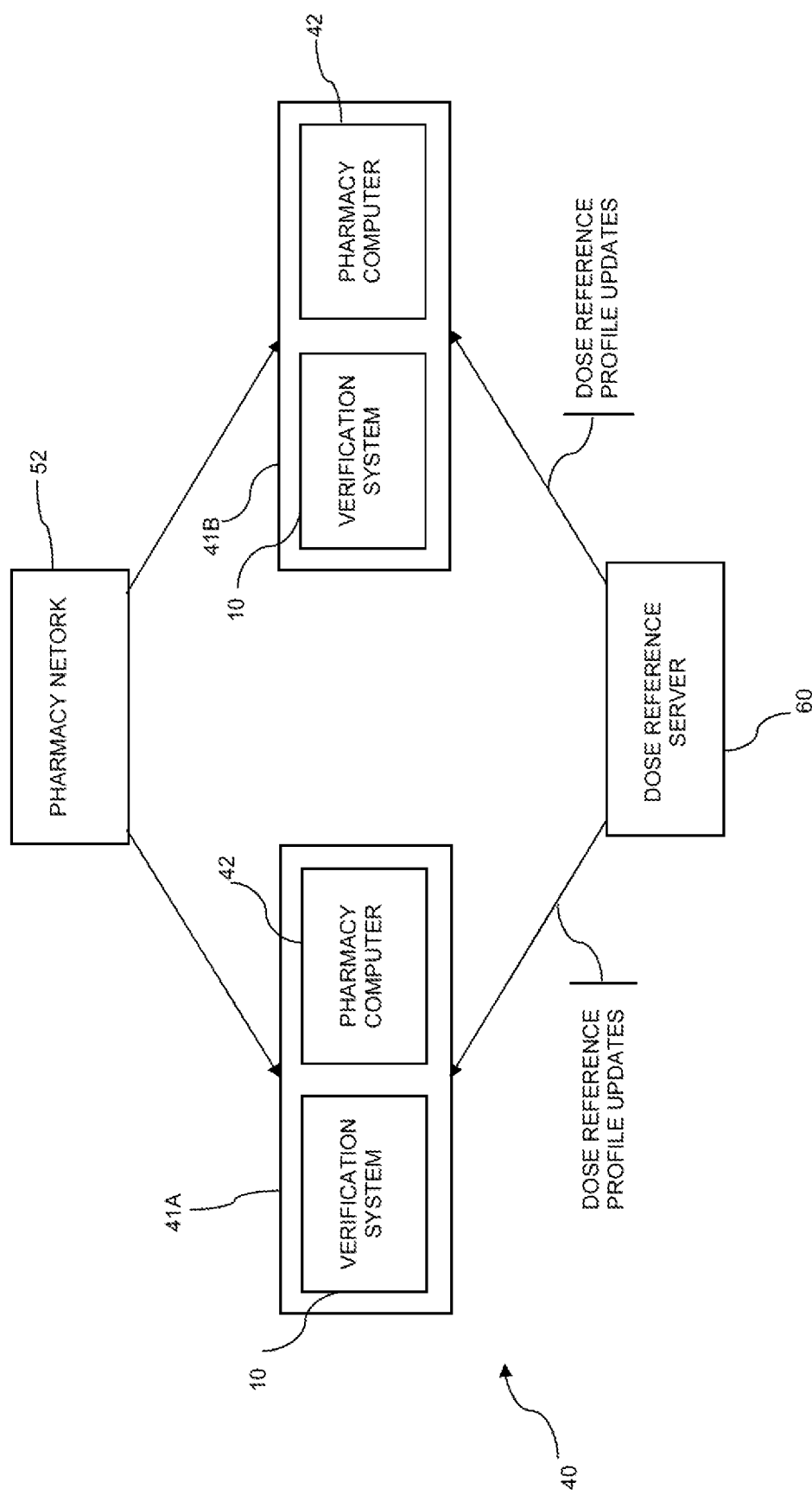
FIG. 2 is a block diagram of verification systems of FIG. 1, in conjunction with a pharmacy network.

Referring to FIG. 2, there is illustrated at 40 a network arrangement for multiple verification systems 10. In FIG. 2, the verification systems 10 are shown as being present in two pharmacies, namely 41A and 41B, although numerous other verification systems may be present in other pharmacies in the same network.

Each pharmacy has in addition to the verification system 10 a pharmacy computer 42, that performs the usual tasks related to prescriptions and pharmacy management: e.g. maintaining and updating patient profiles, managing inventory, etc. The verification system 10 and the pharmacy computer 42 may be share a single processor or may be two separate units. If the verification system 10 and the pharmacy computer 42 are a single processor, the verification unit 12 is part of a software performing the afore-mentioned features.

The pharmacy computers 42 are connected to a pharmacy network 50. For instance, the pharmacy network 50 may keep patient prescription profiles, provide medication updates, etc.

The verification systems 10 are connected to a dose reference server 60 in a client-server model. The dose reference server 60 is used to maintain a master of dose reference profiles. Therefore, the dose reference server is operated to store updated visual parameters for medication, for instance in visual format, as well as all relevant information related to the medication (e.g. bar codes, data matrix, new formats, new doses). The dose reference server 60 provides updates to the verification systems 10, in the form of updated or new dose reference profiles, additional or updated information for existing profiles, etc.

The visual characteristics database 21 of the verification systems 10 (FIG. 1) may thus be continuously updated with the profiles from the dose reference server 60. According to another embodiment, the verification systems 10 obtain dose reference profiles on a per-verification basis. For instance, a verification system 10 may download specific dose reference profiles upon identifying the expected medication of a patient prescription profile, for subsequent verification. The dose reference server 60 may also or alternatively provide the relevant information to or through the pharmacy computer 42.

Figure 3:
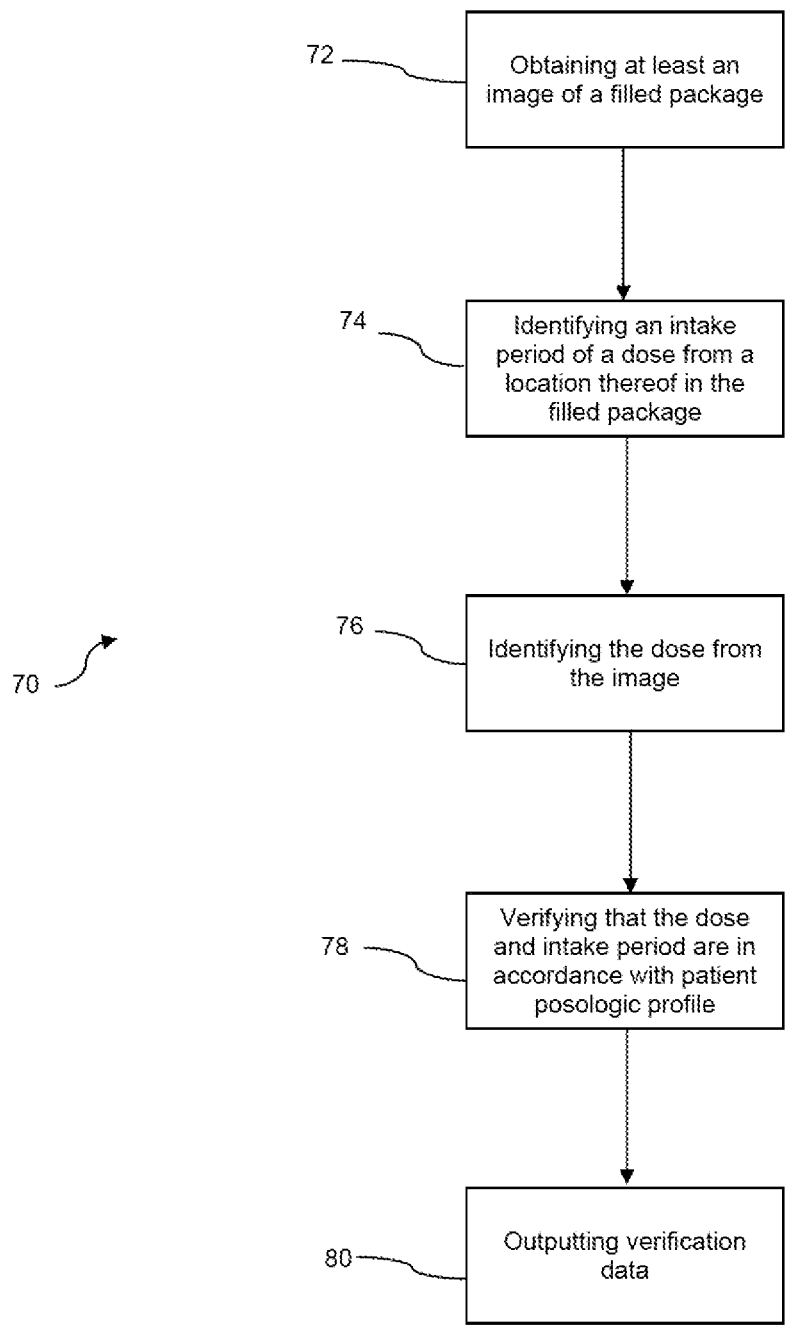
FIG. 3 is a flow chart of a method for verifying the contents of a medication packaging in accordance with another embodiment of the present disclosure.

Referring to FIG. 3, there is illustrated a method 70 for verifying medication systems in a medication package. The method 70 may be performed using the verification system 10 for some steps.

According to 72, at least one image of a filled package is obtained. The image is a photography or the like taken by an appropriate camera so as to obtain visual characteristics related to the doses in a filled package. The visual characteristics may include any of an outline, a geometry, colors (e.g., tint, contrast), brand, bar code, data matrix and any other appropriate type of identification information.

According to 74, an intake period for the doses of the filled package is identified, for one or more of the doses. In an embodiment, the filled package comprises a plurality of compartments each related to an intake period. The image of step 72 may be used to identify the location of the dose and hence an intake period. To identify the intake period, coordinates related to the image may be interpreted as representing an intake period. The coordinates are related to the position of an imaging unit when taking pictures, with each set of coordinates being associated with an intake period. Alternatively, the image may be segmented by compartment in accordance with a grid representing the filled package, with each box of the grid corresponding to a compartment, and thus to an intake period. Therefore, as each segment of the image is associated to a box of the grid, an intake period is tagged to each of the doses in the compartment.

It may also be considered to provide data for each compartment (e.g., bar code, data matrix, characters for OCR), in such a way that the identification of the intake period for each dose is performed by the recognition of the data from the image of 72.

According to 76, the dose is identified from the image. The identification may consist in the comparison of the visual characteristics of the doses from the images with dose reference profiles from a database.

According to an embodiment, the identification may be the comparison of the dose with images of a database of expected doses at the given intake period. In such a case, the identification of the doses is initiated by an identification of the filled package to a patient file, for instance using visual data obtained from the image of 72 (e.g., bar code, data matrix, characters for OCR), or by any other scanning step by an operator, or by manual data entry by the operator. Once the patient file is identified, the patient posologic profile may be received along with visual characteristics of the doses, for the comparison with the imaged doses.

According to 78, the identified dose and the intake period are compared to the patient posologic profile in order to determine that the filled package is correctly filled. The comparison may consist of the creation of a list of identified doses as a function of intake period, adjacent to the same information as obtained from the patient posologic profile.

According to 80, verification data is output to indicate that the package is correctly filled or that there may be errors and that further identification is required.

The invention claimed is:

1. A computer-assisted method for verifying medication doses in a filled medication package as a function of a prescription, comprising:

obtaining a filled medication package having a plurality of compartments, the plurality of compartments arranged in the filled medication package to define a plurality of rows, with each said row comprising a plurality of compartments to form a grid of compartments, each compartment in the grid being assigned an intake period and a dose of medication consisting of a plurality of pills in accordance with the prescription, the plurality of pills including different types of pills, wherein at least a single one of the plurality of compartments has different types therein;

obtaining, using a processor of a computer system, at least one image of the filled medication package;

determining, using the processor of the computer system, the intake period of at least one of the compartments from the at least one image using a location in the grid of the compartment;

determining, using the processor of the computer system, an identity of each imaged pill within said compartment by comparing each imaged pill from the at least one image to visual characteristics of known pill reference profiles;

comparing, using the processor of the computer system, the identity and the intake period of each imaged pill with the prescription, each imaged pill including all of the plurality of pills including different types of pills; and outputting, using the processor of the computer system, data related to the comparing in a visual format to an operator, and indicating to an operator an error requiring additional verification.

2. The computer-assisted method according to claim 1, wherein obtaining at least one image includes obtaining at least two images and creating at least one of a three-dimensional image and a mosaic for subsequent steps.

3. The computer-assisted method according to claim 1, wherein determining the intake period includes identifying the compartment of the imaged pill in the filled medication package and associating a day and hour value to the compartment.

4. The computer-assisted method according to claim 1, wherein determining the intake period comprises reading location data related to the at least one compartment in the filled medication package.

5. The computer-assisted method according to claim 1, further including obtaining a patient posologic profile related to the prescription, and wherein comparing includes comparing the identity and the intake period of the imaged pill with the patient posologic profile.

6. The computer-assisted method according to claim 5, further including obtaining pill reference profiles for medication indicated in the patient posologic profile, and wherein comparing includes comparing the visual characteristics of the imaged pill with data of the obtained pill reference profiles.

7. The computer-assisted method according to claim 5, wherein obtaining the patient posologic profile includes obtaining the patient posologic profile from a pharmacy network.

8. The computer-assisted method according to claim 5, wherein obtaining the patient posologic profile includes scanning data on the filled medication package to obtain identification data to obtain the patient posologic profile from a database.

9. The computer-assisted method according to claim 1, wherein obtaining at least one image of the filled medication package includes obtaining coordinates from a camera producing the image, and wherein determining an intake period includes determining the intake period using the coordinates.

10. The computer-assisted method according to claim 1, including storing, using the processor of the computer system, the at least one image with the prescription, for subsequent use.

11. The computer-assisted method according to claim 1, wherein determining, using the processor of the computer system, the intake period of the at least one of the compartments includes determining the intake period of all of the compartments in the grid of the filled medication package.

12. The computer-assisted method according to claim 1, wherein obtaining at least one image of the filled medication package includes imaging the filled medication package.

13. The computer-assisted method according to claim 12, wherein imaging the filled medication package includes imaging the filled medication package with lighting conditions matching those at a creation of dose reference profiles.

14. The computer-assisted method according to claim 1, wherein outputting data includes indicating to an operator that each said compartment of the filled medication package is correctly filled at the pharmacy.

15. The computer-assisted method according to claim 1, wherein all steps of the method are performed in pharmacy.

16. The computer-assisted method according to claim 12, wherein imaging the filled medication package includes imaging the filled medication package from above the filled medication package.

17. The computer-assisted method according to claim 12, wherein imaging the filled medication package includes imaging the filled medication package in pharmacy.

18. The computer-assisted method according to claim 12, wherein all steps of the method are performed in pharmacy.

19. A computer-assisted method for verifying medication doses in a filled medication package as a function of a prescription, comprising:

imaging a filled medication package having a plurality of compartments, the plurality of compartments arranged in the filled medication package to define a plurality of rows, with each said row comprising a plurality of compartments to form a grid of compartments, each compartment in the grid being assigned an intake period and a dose of medication consisting of a plurality of pills in accordance with the prescription, the plurality of pills including different types of pills in at least one of the plurality of compartments, wherein imaging the filled medication package includes imaging the filled medication package in a similarity condition as at a creation of dose reference profiles;

obtaining, using a processor of a computer system, at least one image of the filled medication package;

determining, using the processor of the computer system, the intake period of at least one of the compartments from the at least one image using a location in the grid of the compartment;

determining, using the processor of the computer system, an identity of each imaged pill within said compartment by comparing each imaged pill from the at least one image to visual characteristics of known pill reference profiles;

comparing, using the processor of the computer system, the identity and the intake period of each imaged pill with the prescription, each imaged pill including all of the plurality of pills including different types of pills; and outputting, using the processor of the computer system, data related to the comparing in a visual format to an operator, and indicating to an operator an error requiring additional verification.

* * * * *